United States Patent
Liang et al.

(10) Patent No.: US 11,540,983 B2
(45) Date of Patent: Jan. 3, 2023

(54) HAIR TREATMENT COMPOSITIONS

(71) Applicant: L'OREAL, Paris (FR)

(72) Inventors: Jun Liang, Staten Island, NY (US); Heather Yoonsoo Lee, Wayne, NJ (US); Dongcui Li, Metuchen, NJ (US)

(73) Assignee: L'OREAL, Paris (FR)

( * ) Notice: Subject to any disclaimer, the term of this patent is extended or adjusted under 35 U.S.C. 154(b) by 90 days.

(21) Appl. No.: 17/218,591

(22) Filed: Mar. 31, 2021

(65) Prior Publication Data
US 2021/0299006 A1 Sep. 30, 2021

Related U.S. Application Data

(60) Provisional application No. 63/002,690, filed on Mar. 31, 2020.

(30) Foreign Application Priority Data

May 7, 2020 (FR) ...................... 2004515

(51) Int. Cl.
| | |
|---|---|
| *A61Q 5/12* | (2006.01) |
| *A61K 8/06* | (2006.01) |
| *A61K 8/34* | (2006.01) |
| *A61K 8/81* | (2006.01) |
| *A61K 8/891* | (2006.01) |
| *A61K 8/898* | (2006.01) |
| *A61K 8/86* | (2006.01) |
| *A61K 8/39* | (2006.01) |
| *A61K 8/41* | (2006.01) |

(52) U.S. Cl.
CPC ................ *A61K 8/062* (2013.01); *A61K 8/34* (2013.01); *A61K 8/342* (2013.01); *A61K 8/345* (2013.01); *A61K 8/347* (2013.01); *A61K 8/39* (2013.01); *A61K 8/416* (2013.01); *A61K 8/817* (2013.01); *A61K 8/8182* (2013.01); *A61K 8/86* (2013.01); *A61K 8/891* (2013.01); *A61K 8/898* (2013.01); *A61Q 5/12* (2013.01); *A61K 2800/524* (2013.01); *A61K 2800/5426* (2013.01); *A61K 2800/805* (2013.01)

(58) Field of Classification Search
CPC .......... A61Q 5/12; A61K 8/416; A61K 8/342; A61K 8/891; A61K 2800/5426; A61K 8/345; A61K 8/34; A61K 8/585; A61K 8/375; A61K 8/25; A61K 2800/31; A61K 2800/898; A61K 8/86
USPC .......................................................... 424/70.1
See application file for complete search history.

(56) References Cited

U.S. PATENT DOCUMENTS

| | | |
|---|---|---|
| 7,476,393 B2 | 1/2009 | Dubief et al. |
| 10,265,251 B2 | 4/2019 | Glenn, Jr. et al. |
| 2012/0003172 A1* | 1/2012 | Desenne ................. A61Q 5/12 424/70.9 |
| 2016/0374910 A1 | 12/2016 | Halpern Chirch et al. |
| 2018/0311140 A1* | 11/2018 | Perner ...................... A61K 8/44 |
| 2018/0338900 A1* | 11/2018 | Patterson ................ A45D 7/04 |
| 2019/0298623 A1 | 10/2019 | Patel et al. |
| 2019/0350823 A1 | 11/2019 | Landa et al. |
| 2019/0374446 A1 | 12/2019 | Valverde et al. |
| 2020/0206111 A1 | 7/2020 | Lee et al. |

* cited by examiner

*Primary Examiner* — Eisa B Elhilo
(74) *Attorney, Agent, or Firm* — Polsinelli PC

(57) ABSTRACT

A hair treatment compositions including about 20 wt. % or more of a polyol; about 5 wt. % to about 50 wt. % of a monoalcohol having 1 to 10 carbons; about 0.1 to about 5 wt. % of silicone; about 0.1 to about 10 wt. % of a cationic polymer; about 0.1 to about 10 wt. % of a cationic surfactant; about 0.1 to about 15 wt. % of a fatty alcohol; and about 10 wt. % or less of water, wherein all percentages by weight are based on the total weight of the hair treatment composition.

20 Claims, No Drawings

HAIR TREATMENT COMPOSITIONS

CROSS-REFERENCE TO RELATED APPLICATIONS

This application claims priority (under 35 U.S.C. 119(e)) of U.S. Provisional Application No. 63/002,690, filed Mar. 31, 2020, and claims priority (under 35 U.S.C. 119(a)) of French Application No. 2004515, filed on May 7, 2020, which are both incorporated herein by reference in their entirety.

FIELD OF THE DISCLOSURE

The instant disclosure relates to hair treatment compositions and, particularly, hair treatment compositions comprising a silicone.

BACKGROUND OF THE DISCLOSURE

Many individuals suffer from dry and damaged hair. Dryness and damage can occur due to several factors including weather exposure, mechanical treatments (e.g. brushing hair), excessive treatments using chemicals, dying hair, heat styling, etc. In combination, using cleansing products that can be excessively stripping of hair's natural oils, can also lead to split ends, dull hair, and exacerbate dry hair. To mitigate the damage, oil treatments, conditioner, hair masks, and chemical treatments are commonly used.

The popularity and usage of oils for dry hair treatments has increased due to their effectiveness and simplicity. Commonly used oils include olive oil, mineral oil, avocado oil, apricot kernel oil, rice bran oil, and coconut oil. However, one problem is that effects are not usually seen after more than several hours (e.g. 8 hours) of treatment and several treatments are usually required, making it time consuming and labor intensive.

Individuals desire a treatment for hair or damaged hair that is not time consuming and labor intensive to use. A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

However, there is still a need for developing new and improved formulations and methods of treating hair for providing improved hair manageability, for example, improved hair alignment, reduced unwanted volume (especially reduced frizz), and increased shine.

SUMMARY OF THE DISCLOSURE

The instant disclosure relates to hair treatment compositions and, particularly, hair treatment compositions comprising a silicone. The hair treatment compositions provide unique sensorial experiences and, advantageously, provide enhanced deposition of silicone. For example, the hair treatment compositions may be a translucent or clear composition containing suspended silicone until the hair treatment composition is combined with extraneous water, whereupon the hair treatment compositions form an opaque emulsion.

The hair treatment compositions typically include:
(a) about 20 wt. % or more of a polyol;
(b) about 5 wt. % to about 50 wt. % of a monoalcohol having 1 to 10 carbons;
(c) about 0.1 to about 5 wt. % of silicone;
(d) about 0.1 to about 5 wt. % of a cationic polymer; and
(e) about 0.1 to about 5 wt. % of a cationic surfactant;
(f) about 0.1 to about 15 wt. % of a fatty alcohol;
(g) about 10 wt. % or less of water,
wherein all percentages by weight are based on the total weight of the hair treatment composition.

The hair treatment composition may be formulated to such that the weight ratio of the polyol to the monoalcohol is from 20:1 to 1:1. In some instances, the hair treatment composition may have a viscosity of about 1 mPa.S to about 10,000 mPa.S at 25° C. at a shear rate of $1s^{-1}$ before combination with extraneous water.

Non-limiting examples of the polyol include those chosen from ethylene glycol, propylene glycol, butylene glycol, hexylene glycol, pentylene glycol, diethylene glycol, dipropylene glycol, 1,3 propanediol, glycerin, diglycerin, polyethylene glycols, and a mixture thereof. In some instances, the polyol is chosen from propylene glycol, dipropylene glycol, glycerin, or a mixture thereof. Suitable examples of the monoalcohol include those having 1 to 10 carbons. In some instances, the monoalcohol is chosen from ethanol, propanol, butanol, pentanol, hexanol, isopropyl alcohol, cyclohexanol, isobutyl alcohol, 2-methyl-2-butanol (2-methylbutan-2-ol), and a mixture thereof.

The hair treatment composition includes a silicone that may be chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, and mixtures thereof.

Examples of suitable cationic polymers include those chosen from polyquaternium-1; polyquaternium-2; polyquaternium-4; polyquaternium-5; polyquaternium-6; polyquaternium-7; polyquaternium-8; polyquaternium-9; polyquaternium-10; polyquaternium-11; polyquaternium-12; polyquaternium-13; polyquaternium-14, polyquaternium-15; polyquaternium-16; polyquaternium-17; polyquaternium-18; polyquaternium-19; polyquaternium-20; polyquaternium-22; polyquaternium-24; polyquaternium-27; polyquaternium-28; polyquaternium-29; polyquaternium-30; polyquaternium-31 polyquaternium-32; polyquaternium-33; polyquaternium-34; polyquaternium-35; polyquaternium-36; polyquaternium-37; polyquaternium-39; polyquaternium-42; polyquaternium-43; polyquaternium-44; polyquaternium-45; polyquaternium-46; polyquaternium-47; polyquaternium-67; and mixtures thereof. In at least one preferable instance, the cationic polymer is polyquaternium-67.

Non-limiting examples of cationic surfactants that may be included in the hair treatment composition include those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

The hair treatment composition includes a fatty alcohol chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, and a mixture thereof.

Additionally and/or alternatively, the hair treatment composition may include about 0.1 to about 5 wt. % of a film former. In some instances, the silicone is suspended within the translucent or clear composition before being combined with extraneous water.

The instant disclosure also relates to methods for treating or improving hair. A method for treating hair typically includes:
  (i) optionally, applying a shampoo to the hair;
  (ii) applying a hair treatment composition to hair, the hair treatment composition comprising:
    (a) about 20 wt. % or more of a polyol;
    (b) about 5 wt. % to about 50 wt. % of a monoalcohol having 1 to 10 carbons;
    (c) about 0.1 to about 5 wt. % of silicone;
    (d) about 0.1 to about 5 wt. % of a cationic polymer; and
    (e) about 0.1 to about 5 wt. % of a cationic surfactant;
    (f) about 0.1 to about 15 wt. % of a fatty alcohol;
    (g) about 10 wt. % or less of water,
      wherein all percentages by weight are based on the total weight of the hair treatment composition;
  (iii) optionally, applying a conditioner to the hair; and
  (iv) optionally, rinsing the hair treatment composition from the hair.

The method for treating hair may include using a hair treatment composition that is a translucent or clear composition until combined with extraneous water, whereupon the hair treatment composition forms an opaque emulsion in situ. Preferably, the method for treating hair may condition the hair; provide curl definition to the hair; provide frizz control to the hair; improve ease of combability and detangling; protect the hair from damage; and/or increase the appearance of the hair volume.

Additionally or alternatively, the method may include one or more of the following steps:
  mixing with a shampoo prior to application to hair;
  layering onto hair with a shampoo;
  applying to hair after a shampoo has been rinsed from the hair;
  layering onto hair with a conditioner;
  mixing with a conditioner prior to application to hair;
  applying to hair after a conditioner has been rinsed from the hair;
  mixing with a leave-in hair treatment prior to application to hair;
  mixing with a mask composition prior to application to hair; or
  applying to hair after a mask composition has been applied to and optionally, rinsed from the hair.

DETAILED DESCRIPTION OF THE DISCLOSURE

The instant disclosure relates to hair treatment compositions and, particularly, hair treatment compositions comprising a silicone. The hair treatment compositions provide unique sensorial experiences and, advantageously, provide enhanced deposition of silicone. The hair treatment compositions are typically suspensions containing a silicone and are translucent or clear prior to use when the hair treatment composition is combined with extraneous water.

The hair treatment compositions typically include:
  (a) about 20 wt. % or more of a polyol;
  (b) about 5 wt. % to about 50 wt. % of a monoalcohol having 1 to 10 carbons;
  (c) about 0.1 to about 5 wt. % of silicone;
  (d) about 0.1 to about 5 wt. % of a cationic polymer; and
  (e) about 0.1 to about 5 wt. % of a cationic surfactant;
  (f) about 0.1 to about 15 wt. % of a fatty alcohol;
  (g) about 10 wt. % or less of water,
    wherein all percentages by weight are based on the total weight of the hair treatment composition.

During use, a user combines the hair treatment composition with extraneous water (e.g., water other than the water already included in the hair treatment composition). As the hair treatment composition becomes mixed with extraneous water, the composition becomes opaque. This can occur, for example, when a consumer applies the hair treatment composition to a wet or damp part of the body (e.g., hands, face, skin, hair, etc.). The user may then physically manipulate the applied hair treatment composition (for example, by rubbing the hands together or rubbing the composition against another part of the body such as the face, hair, etc.).

The hair treatment composition forms an opaque emulsion upon combination with extraneous water, for example, from a user's wet or damp hands, wet or damp hair, and/or from the faucet and the like. The opaque emulsion may be formed by combining extraneous water with the hair treatment composition in an ratio (water:composition) ranging from 0.1:1 to 3:1, preferably 0.5:1 or 1:1 or 1.5:1 or 2:1. Additionally and/or alternatively, the opaque emulsion may be formed by combining extraneous water in an amount such that the total amount of water in the hair treatment composition increases to more than 10 wt. % or, in some instances, to 12 wt. % or more, 15 wt. % or more, 20 wt. % or more, 25 wt. % or more, or 30 wt. % or more, based on the total weight of the hair treatment composition before combination with extraneous water.

The opaque emulsion formed from the combination of the hair treatment composition and extraneous water may occur with mixing from the user. For example, in some instances, the opaque emulsion is formed automatically without the need for mixing. In other words, the hair treatment composition becomes sufficiently combined with extraneous water to form the opaque emulsion by simply coming into contact with extraneous water. In some instances, however, a minimal amount of mixing may be needed, and may be encouraged, to more thoroughly form the opaque emulsion. This can easily be achieved during use of the hair treatment composition, for example, by physically manipulating (e.g., mixing) the hair treatment composition with extraneous water using the body (e.g., with the hands).

The hair treatment composition may be formulated to have an amount of polyol to an amount of monoalcohols in a ratio (i.e. total polyols:total monoalcohols) of 20:1 to 1:1. For example, the ratio of the amount of polyols to the amount of monoalcohols having from 2 to 6 carbon atoms may be from 20:1 to 1:1, 18:1 to 1:1, 15:1 to 1:1, 10:1 to 1:1, 7:1 to 1:1, 6:1 to 1:1, 5:1 to 1:1, or 4:1 to 1.1:1, including ranges and sub-ranges therebetween. In at least one embodiment, the hair treatment composition is formulated such that the total amount of polyols is greater than the total amount of monoalcohols.

As used herein, the term "translucent" with respect to a translucent composition indicates that the composition has transmittance of at least 50% at a wavelength of 600 nm, for example measured using a Lambda 40 UV-visible spectrometer. A translucent hair treatment compositions may have, for example, a transmittance of at least 50%, 60%, or at least 70% at a wavelength of 600 nm, measured, for example, using a Lambda 40 UV-visible spectrometer. Additionally, the term "clear," as used herein, refers to a composition having a transmittance of at least at least 80% at a wavelength of 600 nm, for example, measured using a Lambda 40 UV-visible spectrometer. For example, a clear hair treatment composition may have a transmittance of at least 80%, 90% or at least 95% at a wavelength of 600 nm, for example, measured using a Lambda 40 UV-visible spectrometer. Without being limited to any particular theory, typically clear hair treatment compositions are nanoemulsions or microemulsions, while translucent hair treatment compositions typically are macroemulsions.

The hair treatment compositions typically have a viscosity of about 1 mPa.s to about 10,000 mPa.s at 25° C. before combination with extraneous water. For example, the hair treatment compositions may have a viscosity of about 1 mPa.s to about 10,000 mPa.s, about 1 mPa.s to about 8,000 mPa.s, about 1 mPa.s to about 6,000 mPa.s, about 1 mPa.s to about 5,000 mPa.s, about 1 mPa.s to about 4,000 mPa.s, about 1 mPa.s to about 3,000 mPa.s; about 10 mPa.s to about 10,000 mPa.s, about 10 mPa.s to about 8,000 mPa.s, about 10 mPa.s to about 6,000 mPa.s, about 10 mPa.s to about 5,000 mPa.s, about 10 mPa.s to about 4,000 mPa.s, about 10 mPa.s to about 3,000 mPa.s; 500 mPa.s to about 10,000 mPa.s, about 500 mPa.s to about 8,000 mPa.s, about 500 mPa.s to about 6,000 mPa.s, about 500 mPa.s to about 5,000 mPa.s, about 500 mPa.s to about 4,000 mPa.s, about 50 mPa.s to about 3,000 mPa.s; about 1,000 mPa.s to about 10,000 mPa.s, about 1,000 mPa.s to about 8,000 mPa.s, about 1,000 mPa.s to about 6,000 mPa.s, about 1,000 mPa.s to about 5,000 mPa.s, about 1,000 mPa.s to about 4,000 mPa.s, about 1,000 mPa.s to about 3,000 mPa.s; about 2,000 mPa.s to about 10,000 mPa.s, about 2,000 mPa.s to about 8,000 mPa.s, about 2,000 mPa.s to about 6,000 mPa.s, about 2,000 mPa.s to about 5,000 mPa.s, about 2,000 mPa.s to about 4,000 mPa.s, about 2,000 mPa.s to about 3,000 mPa.s, at a temperature of 25° C. before combination with extraneous water. The viscosity measurements can be carried out, for example, using a Brooksfield viscometer, Model RVT (Brookfield Engineering Laboratories, Inc.) at about 60 revolutions per minute (RPM), at ambient room temperature of about 20 to 25° C.; spindle sizes may be selected in accordance with the standard operating recommendations form the manufacturer, ranging from disk spindle No. 1 to No. 4.

Suitable components, such as those listed below, may be included or excluded from the formulations for the hair treatment compositions depending on the specific combination of other components, the form of the hair treatment compositions, and/or the use of the formulation (e.g., a lotion, gel, cream, spray, etc.).

Polyol(s)

The hair treatment compositions include one or more polyols, e.g., such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof. The amount of polyol(s) present in the hair treatment composition typically ranges from about 20 wt. % or more, based on the total weight of the hair treatment composition. For example, the amount of polyol(s) in the hair treatment composition may be about 20 to about 88 wt. %, about 20 to about 85 wt. %, about 20 to about 80 wt. %, about 20 to about 75 wt. %, about 20 to about 70 wt. %, about 20 to about 65 wt. %, about 20 to about 60 wt. %, about 20 to about 55 wt. %, about 20 to about 50 wt. %, about 20 to about 45 wt. %, about 20 to about 40 wt. %, about 20 to about 35 wt. %, about 20 to about 30 wt. %; about 25 to about 88 wt. %, about 25 to about 85 wt. %, about 25 to about 80 wt. %, about 25 to about 75 wt. %, about 25 to about 70 wt. %, about 25 to about 65 wt. %, about 25 to about 60 wt. %, about 25 to about 55 wt. %, about 25 to about 50 wt. %, about 25 to about 45 wt. %, about 25 to about 40 wt. %, about 25 to about 35 wt. %; about 30 to about 85 wt. %, about 30 to about 80 wt. %, about 30 to about 75 wt. %, about 30 to about 70 wt. %, about 30 to about 65 wt. %, about 30 to about 60 wt. %, about 30 to about 55 wt. %, about 30 to about 50 wt. %, about 30 to about 45 wt. %, about 30 to about 40 wt. %; about 40 to about 87 wt. %, about 40 to about 85 wt. %, about 40 to about 80 wt. %, about 40 to about 75 wt. %, about 40 to about 70 wt. %, about 40 to about 65 wt. %, about 40 to about 60 wt. %, about 40 to about 55 wt. %, about 40 to about 50 wt. %; about 50 to about 87 wt. %, about 50 to about 85 wt. %, about 50 to about 80 wt. %, about 50 to about 75 wt. %, about 50 to about 70 wt. %, about 50 to about 65 wt. %, about 50 to about 60 wt. %; about 60 to about 87 wt. %, about 60 to about 85 wt. %, about 60 to about 80 wt. %, about 60 to about 75 wt. %, about 60 to about 70 wt. %; about 65 to about 87 wt. %, about 65 to about 85 wt. %, about 65 to about 80 wt. %, about 65 to about 75 wt. %; about 70 to about 87 wt. %, about 70 to about 85 wt. %, about 70 to about 75 wt. %, including all ranges and sub-ranges therebetween, based on the total weight of the hair treatment composition.

The term "polyol" should be understood as meaning, within the meaning of the present disclosure, an organic molecule comprising at least two free hydroxyl groups. The polyols of the hair treatment composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair treatment composition, in certain instances, include ethylene glycol, propylene glycol, butylene glycol, hexylene glycol, pentylene glycol, 1,3-propanediol, dipropylene glycol, caprylyl glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair treatment composition comprises at least propylene glycol, and optionally one or more polyols other than propylene glycol.

Non-limiting examples of polyols that may be included in the hair treatment include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol.

Monoalcohol(s)

The hair treatment compositions include monoalcohol(s), such as those having from 2 to 6 carbon atom. The amount of monoalcohol present in the hair treatment composition may range from about 5 to about 50 wt. %, based on the total weight of the hair treatment composition. For example, the hair treatment composition may have monoalcohol in an amount of about 5 to about 50 wt. %, about 5 to about 45 wt. %, about 5 to about 40 wt. %, about 5 to about 35 wt. %, about 5 to about 30 wt. %, about 5 to about 25 wt. %; about 10 to about 50 wt. %, about 10 to about 45 wt. %, about 10 to about 40 wt. %, about 10 to about 35 wt. %, about 10 to about 30 wt. %, about 10 to about 25 wt. %; about 15 to about 50 wt. %, about 15 to about 45 wt. %, about 15 to about 40 wt. %, about 15 to about 35 wt. %, about 15 to about 30 wt. %, or about 15 to about 25 wt. % including all ranges and sub-ranges therebetween, based on the total weight of the hair treatment composition.

The one or more monoalcohols of the hair treatment composition may be chosen from ethanol, propanol, butanol, pentanol, hexanol, isopropyl alcohol, cycohexanol, isobutyl alcohol, 2-methyl-2-butanol (2-methylbutan-2-ol), and a mixture thereof. In one instance, the one or more monoalcohol(s) includes or consists of ethanol.

The hair treatment composition may be formulated to have an amount of polyols to the amount of monoalcohols that is from 20:1 to 1:1, 18:1 to 1:1, 15:1 to 1:1, 10:1 to 1:1, 7:1 to 1:1, 6:1 to 1:1, 5:1 to 1:1, or 4:1 to 1.1:1, including ranges and sub-ranges therebetween. Additionally or alternatively, the hair treatment composition may be formulated to have an amount of glycol to an amount of monoalcohols in a ratio (i.e. total glycols:total monoalcohols) of 20:1 to 1:1. For example, the ratio of the amount of glycol to the amount of monoalcohols having from 2 to 6 carbon atoms may be from 20:1 to 1:1, 18:1 to 1:1, 15:1 to 1:1, 10:1 to 1:1, 7:1 to 1:1, 6:1 to 1:1, 5:1 to 1:1, or 4:1 to 1.1:1, including ranges and sub-ranges therebetween. In at least one instance, the hair treatment composition is formulated such that the total amount of polyol is greater than the total amount of monoalcohols.

Silicone(s)

The hair treatment composition includes silicone(s) typically in an amount ranging from about 0.1 to about 5 wt. %, based on the total weight of the hair treatment composition. For example, the amount of silicone(s) present in the hair treatment composition may range from about 0.1 to about 5 wt. %, about 0.1 to about 4 wt. %; about 0.1 to about 3 wt. %; about 0.1 to about 2 wt. %; about 0.5 to about 5 wt. %, about 0.5 to about 4 wt. %; about 0.5 to about 3 wt. %; about 0.5 to about 2 wt. %; about 1 to about 5 wt. %, about 1 to about 4 wt. %; about 1 to about 3 wt. %; about 1 to about 2 wt. %; about 1.5 to about 5 wt. %, about 1.5 to about 4 wt. %, or about 1.5 to about 3 wt. %; about 2 to about 5 wt. %, about 2 to about 4 wt. %, about 2 to about 3 wt. %; about 2.5 to about 5 wt. %, about 2.5 to about 4 wt. %; about 3 to about 5 wt. %, about 3 to about 4 wt. %; about 3.5 to about 5 wt. %, about 3.5 to about 4 wt. %, including all ranges and sub-ranges therebetween, based on the total weight of the hair treatment composition.

The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The hair treatment composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11 Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

The silicone(s) may, optionally, include or be chosen from a siloxane with a methacrylic group on one of its molecular ends, polydimethylsiloxane containing a styryl group on one of its molecular ends, or a similar silicone compound containing unsaturated groups; butadiene; vinyl chloride; vinylidene chloride; methacrylonitrile; dibutyl fumarate; anhydrous maleic acid; anhydrous succinic acid; methacryl glycidyl ether; an organic salt of an amine, an ammonium salt, and an alkali metal salt of methacrylic acid, of itaconic acid, of crotonic acid, of maleic acid or of fumaric acid; a radical-polymerizable unsaturated monomer containing a sulfonic acid group such as a styrenesulfonic acid group; a quaternary ammonium salt derived from methacrylic acid, such as 2-hydroxy-3-methacryloxypropyltrimethylammonium chloride; and a methacrylic acid ester of an alcohol containing a tertiary amine group, such as a methacrylic acid ester of diethylamine.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone.

In some instances, an amino-functionalized silicones is selected from compounds having the following formula:

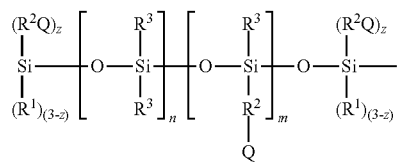

wherein each $R^1$ is independently selected from a $C_{1-30}$ alkyl group, a $C_{1-30}$ alkoxy group, a $C_{5-30}$ aryl group, a $C_{6-30}$ aralkyl group, a $C_{6-30}$ aralkyloxy group, a $C_{1-30}$ alkaryl group, a $C_{1-30}$ alkoxyaryl group, and a hydroxy group (preferably, each $R^1$ is independently selected from a $C_{1-30}$ alkyl group, a $C_{1-30}$ alkoxy group and a hydroxy group);

each $R^2$ is independently a divalent alkylene radical having one to ten carbon atoms (preferably, $R^2$ is a divalent alkylene radical having three to six carbon atoms);

each $R^3$ is independently selected from a $C_{1-30}$ alkyl group, a $C_{5-30}$ aryl group, a $C_{6-30}$ aralkyl group and a $C_{1-30}$ alkaryl group (preferably, each $R^3$ is independently selected from of a $C_{1-30}$ alkyl group);

Q is a monovalent radical selected from $—NR^4_2$ and $—NR^4(CH_2)_xNR^4_2$;

each $R^4$ is independently selected from a hydrogen and a $C_{1-4}$ alkyl group;

x is 2 to 6;

z is 0 or 1;

n is 25 to 3,000 (preferably, 25 to 2,000; more preferably, 25 to 1,000; most preferably 25 to 500); and m is 0 to 3,000 (preferably, 0 to 2,000; more preferably, 0 to 1,000; most preferably, 0 to 100);

with the proviso that at least 50 mol % of the total number of $R^1$ and $R^3$ groups are methyl and with the proviso that when m is 0, z is 1.

Preferred $R^1$ groups include methyl, methoxy, ethyl, ethoxy, propyl, propoxy, isopropyl, isopropoxy, butyl, butoxy, isobutyl, isobutoxy, phenyl, xenyl, benzyl, phenylethyl, tolyl and hydoxy. Preferred $R^2$ divalent alkylene radicals include trimethylene, tetramethylene, pentamethylene, $—CH_2CH(CH_3)CH_2—$ and $—CH_2CH_2CH(CH_3)CH_2—$. Preferred $R^3$ groups include methyl, ethyl, propyl, isopropyl, butyl, isobutyl, phenyl, xenyl, benzyl, phenylethyl and tolyl. Preferred $R^4$ groups include methyl, ethyl, propyl, isopropyl, butyl and isobutyl. When z is 0, the amino-functionalized silicine has only pendant amine functional substituents in the polymer chain. When z is 1, the amino-functional silicone may have only terminal amine functional substituents (e.g., m=0) or may have both terminal and pendant amine functional substituents in the polymer chain (e.g., m>0). Preferably, n+m is 50 to 1,000. More preferably, n+m is 50 to 750. Still more preferably, n+m is 50 to 500. Most preferably, n+m is 50 to 250.

In some instances, the amino-functionalized silicones are alkoxylated and/or hydroxylated amino silicones. Suitable alkoxylated and/or hydroxylated amino silicones may be selected from compounds of the following formula:

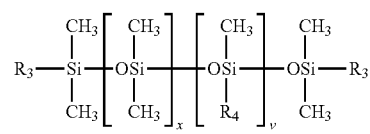

wherein $R_3$ is hydroxyl or $OR_5$, $R_5$ is a $C_1$ to $C_4$ alkyl group, $R_4$ is a group with structure according to the following formula:

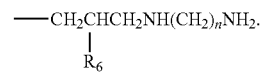

$R_6$ is a $C_1$ to $C_4$ alkyl, n is a 1 to 4, x is the same as "n" described above, and y is the same as "m" described above.

The silicone may be a polysiloxane corresponding to the following formula:

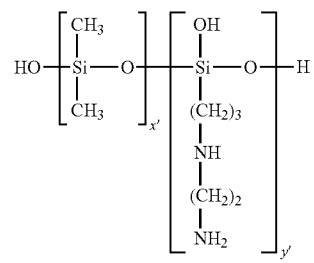

in which x' and y' are integers such that the weight-average molecular weight (Mw) is comprised between about 5000 and 500,000;

b) amino silicones corresponding to following formula:

in which:

G, which may be identical or different, designate a hydrogen atom, or a phenyl, OH or $C_{1-8}$ alkyl group, for example methyl, or $C_{1-8}$ alkoxy, for example methoxy, a, which may be identical or different, denote the number 0 or an integer from 1 to 3, in particular 0;

b denotes 0 or 1, and in particular 1;

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

R', which may be identical or different, denote a monovalent radical having formula -C$_q$H$_{2q}$L in which q is a number ranging from 2 to 8 and L is an optionally quaternized amino group chosen from the following groups:

—NR"-Q-N(R")$_2$
—N(R")$_2$
—N+(R")$_3$A-
—N+H(R")$_2$A-
—N+H$_2$(R")A-
—N(R")-Q-N+R"H$_2$A-
—NR"-Q-N+(R")$_2$H A-
—NR"-Q-N+(R")$_3$ A-, in which R", which may be identical or different, denote hydrogen, phenyl, benzyl, or a saturated monovalent hydrocarbon-based radical, for example a C$_1$-C$_{20}$ alkyl radical; Q denotes a linear or branched C$_r$H$_{2r}$ group, r being an integer ranging from 2 to 6, preferably from 2 to 4; and A- represents a cosmetically acceptable ion, in particular a halide such as fluoride, chloride, bromide or iodide.

Another group of amino silicones corresponding to this definition is represented by silicones having the following formula:

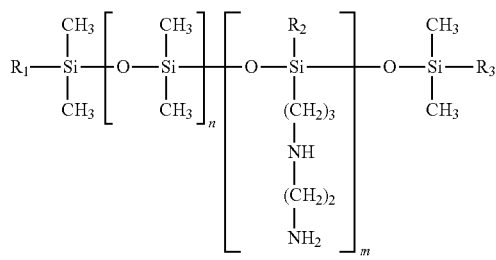

in which:

m and n are numbers such that the sum (n+m) can range from 1 to 1000, in particular from 50 to 250 and more particularly from 100 to 200, it being possible for n to denote a number from 0 to 999 and in particular from 49 to 249, and more particularly from 125 to 175, and for m to denote a number from 1 to 1000 and in particular from 1 to 10, and more particularly from 1 to 5;

R$_1$, R$_2$, R$_3$, which may be identical or different, represent a hydroxy or C$_1$-C$_4$ alkoxy radical, where at least one of the radicals R$_1$ to R$_3$ denotes an alkoxy radical.

The alkoxy radical is preferably a methoxy radical. The hydroxy/alkoxy mole ratio ranges preferably from 0.2:1 to 0.4:1 and preferably from 0.25:1 to 0.35:1 and more particularly equals 0.3:1. The weight-average molecular weight (Mw) of the silicone ranges preferably from 2,000 to 1,000,000, more particularly from 3,500 to 200,000.

Another group of amino silicones corresponding to this definition is represented by the following formula:

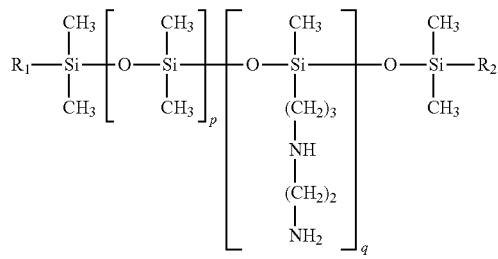

in which:

p and q are numbers such that the sum (p+q) ranges from 1 to 1000, particularly from 50 to 350, and more particularly from 150 to 250; it being possible for p to denote a number from 0 to 999 and in particular from 49 to 349, and more particularly from 159 to 239 and for q to denote a number from 1 to 1000, in particular from 1 to 10, and more particularly from 1 to 5;

R$_1$, R$_2$, which may be the same or different, represent a hydroxy or C$_1$-C$_4$ alkoxy radical, where at least one of the radicals R$_1$ or R$_2$ denotes an alkoxy radical.

The alkoxy radical is preferably a methoxy radical. The hydroxy/alkoxy mole ratio ranges generally from 1:0.8 to 1:1.1 and preferably from 1:0.9 to 1:1 and more particularly equals 1:0.95.

Another group of amino silicones is represented by the following formula:

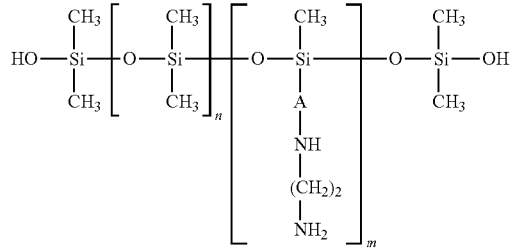

in which:

m and n are numbers such that the sum (n+m) ranges from 1 to 2000 and in particular from 50 to 150, it being possible for n to denote a number from 0 to 1999 and in particular from 49 to 149, and for m to denote a number from 1 to 2000 and in particular from 1 to 10;

A denotes a linear or branched alkylene radical containing from 4 to 8 carbon atoms and preferably 4 carbon atoms. This radical is preferably linear.

The weight-average molecular weight (Mw) of these amino silicones ranges preferably from 2000 to 1,000,000 and even more particularly from 3500 to 200,000.

Another group of amino silicones is represented by the following formula:

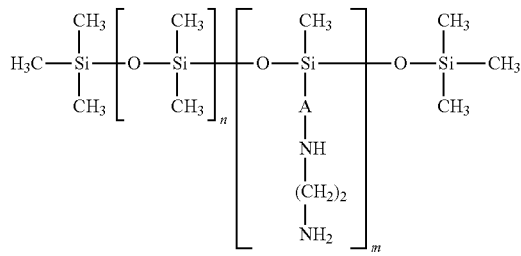

in which:

m and n are numbers such that the sum (n+m) ranges from 1 to 2000 and in particular from 50 to 150, it being possible for n to denote a number from 0 to 1999 and in particular from 49 to 149, and form to denote a number from 1 to 2000 and in particular from 1 to 10;

A denotes a linear or branched alkylene radical containing from 4 to 8 carbon atoms and preferably 4 carbon atoms. This radical is preferably branched.

The weight-average molecular weight (Mw) of these amino silicones ranges preferably from 500 to 1,000,000 and even more particularly from 1000 to 200,000.

Another group of amino silicones is represented by the following formula:

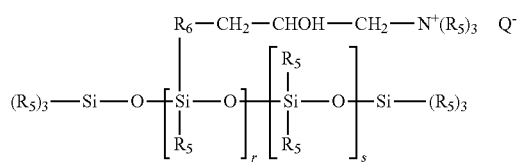

in which:

$R_5$ represents a monovalent hydrocarbon-based radical containing from 1 to 18 carbon atoms, and in particular a $C_1$-$C_{18}$ alkyl or $C_2$-$C_{18}$ alkenyl radical, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

Q- is an anion such as a halide ion, in particular chloride, or an organic acid salt (for example acetate);

r represents a mean statistical value from 2 to 20 and in particular from 2 to 8;

s represents a mean statistical value from 20 to 200 and in particular from 20 to 50.

Such amino silicones are described more particularly in patent U.S. Pat. No. 4,185,087.

A group of quaternary ammonium silicones is represented by the following formula:

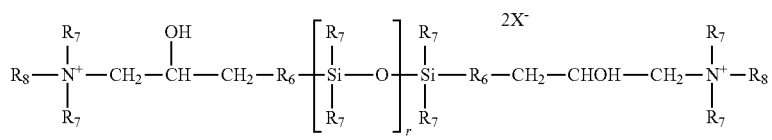

in which:

$R_7$, which may be identical or different, represent a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

X- is an anion such as a halide ion, in particular chloride, or an organic acid salt (for example acetate);

r represents a mean statistical value from 2 to 200 and in particular from 5 to 100. These silicones are described, for example, in patent application EP-A 0530974.

A group of quaternary ammonium silicones is represented by the following formula:

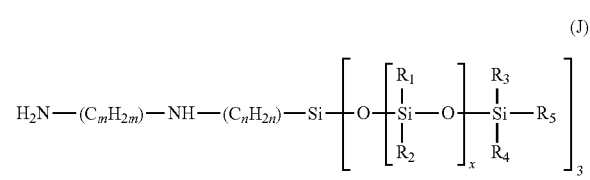

in which:

$R_1$, $R_2$, $R_3$ and $R_4$, which may be identical or different, denote a $C_1$-$C_4$ alkyl radical or a phenyl group;

$R_5$ denotes a $C_1$-$C_4$ alkyl radical or a hydroxyl group;

n is an integer ranging from 1 to 5;

m is an integer ranging from 1 to 5;

and in which x is chosen such that the amine number is between 0.01 and 1 meq/g;

multiblockpolyoxyalkylenated amino silicones, of type (AB)n, A being a polysiloxane block and B being a polyoxyalkylenated block containing at least one amine group.

Said silicones are preferably constituted of repeating units having the following general formulae:

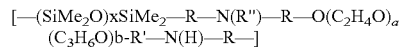

or alternatively

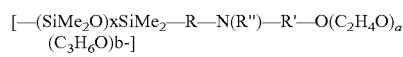

in which:

a is an integer greater than or equal to 1, preferably ranging from 5 to 200, more particularly ranging from 10 to 100;

b is an integer comprised between 0 and 200, preferably ranging from 4 to 100, more particularly between from 5 and 30;

x is an integer ranging from 1 to 10 000, more particularly from 10 to 5000;

R" is a hydrogen atom or a methyl;

R, which may be identical or different, represent a divalent linear or branched $C_2$-$C_{12}$ hydrocarbon-based radical, optionally including one or more heteroatoms such as oxygen; preferably, R denotes an ethylene radical, a linear or branched propylene radical, a linear or branched butylene radical, or a —$CH_2CH_2CH_2OCH(OH)CH_2$— radical; preferentially R denotes a —$CH_2CH_2CH_2OCH(OH)CH_2$— radical;

R', which may be identical or different, represent a divalent linear or branched $C_2$-$C_{12}$ hydrocarbon-based radical, optionally including one or more heteroatoms such as oxygen; preferably, R' denotes an ethylene radical, a linear or branched propylene radical, a linear or branched butylene radical, or a —$CH_2CH_2CH_2OCH(OH)CH_2$— radical; preferentially R' denotes —$CH(CH_3)$—$CH_2$—.

The siloxane blocks preferably represent between 50 and 95 mol % of the total weight of the silicone, more particularly from 70 to 85 mol %.

The amine content is preferably between 0.02 and 0.5 meq/g of copolymer in a 30% solution in dipropylene glycol, more particularly between 0.05 and 0.2.The weight-average molecular weight (Mw) of the silicone oil is preferably comprised between 5000 and 1,000,000, more particularly between 10,000 and 200,000.

The silicone may be selected from those having at least one quaternary ammonium group. Suitable non-limiting examples are quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Preferred are quaternium 80, silicone quaternium-16, silicone quaternium-18, silicone quaternium-1, silicone quaternium-2, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-17, silicone quaternium-20 and silicone quaternium-21. More preferred are quaternium 80, silicone quaternium-16, silicone quaternium-18, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, and silicone quaternium-17. Preferred are quaternium 80, silicone quaternium-16, silicone quaternium-18, silicone quaternium-15, and mixtures thereof. In an embodiment, the one or more silicone oils of the present disclosure is a non-amino silicone oil such as a dimethicone.

Non-limiting examples of am ino-functionalized silicones include bis-hydroxy/methoxy amodimethicones, bis-cetearyl amodimethicone, amodimethicone, bis(C13-15 alkoxy) PG amodimethicones, am inopropyl phenyl trimethicones, am inopropyl dimethicones, bis-amino PEG/PPG-41/3 am inoethyl PG-propyl dimethicones, caprylyl methicones, and a mixture thereof. In some instances, a particularly useful amino-functionalized silicone is bis-hydroxy/methoxy amodimethicone, wherein X is isobutyl and one of the R is OH and the other is $OCH_3$ in the above structure, also known as "Bis-Hydroxy/Methoxy Amodimethicone" and "3-[(2-aminoethyl)amino]-2-methylpropyl Me, di-Me, [(hydroxydimethylsilyl)oxy]- and [(methoxydimethylsilyl)oxy]-terminated." Bis-hydroxy/methoxy amodimethicone is commercially available under the tradename DOWSIL AP-8087 FLUID from The Dow Chemical Company. A non-limiting example of amodimethicone products containing amino silicones having structure (D) re sold by Wacker under the name BELSIL ADM 652, BELSIL ADM 4000 E, or BELSIL ADM LOG 1. A product containing amino silicones having structure (E) is sold by Wacker under the name FLUID WR 1300. Additionally or alternative, the weight-average molecular weight (Mw) of the silicone ranges preferably from 2,000 to 200,000, even more particularly 5,000 to 100,000 and more particularly from 10,000 to 50,000.

The silicone(s) in the hair treatment compositions of the instant disclosure are included in the form of a silicone emulsion comprising at least one silicone and at least one surfactants, for example, nonionic surfactants, cationic surfactants, amphoteric surfactants, anionic surfactants. The silicone emulsions can be nanoemulsions, microemulsions or macroemulsions. Suitable examples of nonionic surfactants are alkoxylated fatty alcohols or polyethylene glycol ethers of mixtures of C8-C30 fatty alcohols with an average of number of moles of ethylene oxide such as C11-15 Pareth-7, laureth-9, laureth-12, deceth-7, deceth-10, trideceth-6, trideceth-10, trideceth-12, or a mixture thereof. Suitable examples of amphoteric surfactants are cocamidopropyl betaine, coco-betaine, or a mixture thereof. Suitable examples of cationic surfactants are quaternary ammonium compounds such as behentrimonium chloride, cetrimoinium chloride, behentrimonium methosulfate, or a mixture thereof. Suitable examples of anionic surfactants are sulfate-based compounds such as further comprises up to 5 wt. % of a surfactant, for example, sodium (or ammonium) lauryl sulfate, sodium(or ammonium) laureth sulfate, or mixtures thereof.

Cationic Polymer(s)

The hair treatment compositions include cationic polymer (s). The amount of cationic polymer(s) may be from about 0.1 to about 10 wt. % of the total weight of the hair treatment composition. In some instances, the cationic polymers are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %,including ranges and sub-ranges therebetween, based on the total weight of the hair treatment composition.

The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methylimidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair treatment composition may include or be chosen from polyquaterniums. For example, the hair treatment composition may include Polyquaternium-1 (ethanol, 2,2', 2"-nitrilotris-, polymer with 1,4-dichloro-2-butene and N,N, N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/ diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylam inoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In some instances, the hair treatment compositions of the instant disclosure include one or more cationic polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful.

The cationic polymers may be a polyquaternium. In certain embodiments, the cationic surfactants may be polyquaternium polymers selected polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

Cationic Surfactant(s)

The hair treatment composition includes a cationic surfactant(s). The amount of cationic surfactant(s) may be from about 0.1 to about 10 wt. % of the total weight of the hair treatment composition. In some instances, the cationic surfactant(s) are in an amount ranging from about 0.1 to about 10 wt. %, about 0.1 to about 8 wt. %, about 0.1 to about 6 wt. %, about 0.1 to about 4 wt. %, about 0.1 to about 3 wt. %; about 0.2 to about 10 wt. %, about 0.2 to about 8 wt. %, about 0.2 to about 6 wt. %, about 0.2 to about 4 wt. %, about 0.2 to about 3 wt. %; about 0.5 to about 10 wt. %, about 0.5 to about 8 wt. %, about 0.5 to about 6 wt. %, about 0.5 to about 4 wt. %, about 0.5 to about 3 wt. %; about 1 to about 10 wt. %, about 1 to about 8 wt. %, about 1 to about 6 wt. %, about 1 to about 4 wt. %, about 1 to about 3 wt. %; about 1.5 to about 10 wt. %, about 1.5 to about 8 wt. %, about 1.5 to about 6 wt. %, about 1.5 to about 4 wt. %, about 1.5 to about 3 wt. %; about 2 to about 10 wt. %, about 2 to about 8 wt. %, about 2 to about 6 wt. %, about 2 to about 4 wt. %, about 2 to about 3 wt. %, including ranges and sub-ranges therebetween, based on the total weight of the hair treatment composition.

In certain embodiments, the cationic surfactants include or are chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases it is useful to use salts such as chloride salts of the quaternary ammonium compounds.

The fatty amines generally comprise at least one $C_8$-$C_{30}$ hydrocarbon-based chain. For example, quaternary ammonium salts, which may be incorporated in certain instances, include those corresponding to the following general formula:

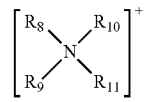

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

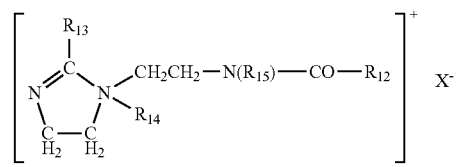

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylaryl-sulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

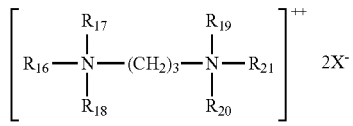

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), Examples of cationic/cationizable surfactants, which may be incorporated in certain instances, include those having a structure in accordance with the general formula provided below:

$R_4$-A-$R_5$-B wherein $R_4$ is a saturated or unsaturated, straight or branched alkyl chain with 8 to 24 C atoms, $R_5$ is a straight or branched alkyl chain with 1 to 4 C atoms, A is selected from:

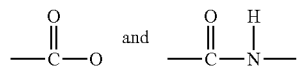

and B is selected from:

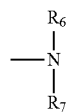

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms,

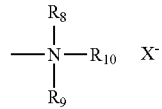

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to Rio are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palm itam idopropyl amine, palm itam idopropyl methylamine, palm itam idopropyl diethylamine, palm itam idopropyl dibutylamine, palm itam idopropyl buylamine, palm itam idopropyl dipropylamine, palm itam idopropyl propylamine, palm itam idopropyl dihydroxyethylamine, palm itam idopropyl hydroxyethylamine, palm itam idopropyl dihydroxypropylamine, palm itam idopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palm itoam idopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palm itylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palm itam idopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereofare useful, especially in combination with fatty dimethylamines such as, for example, stearamidopropyl dimethylamine.

In an embodiment, hair treatment composition may be formulated with a cationic surfactant chosen from behentrimonium chloride, cetrimonium chloride, behentrimonium methosulfate, or mixtures thereof.

The hair treatment composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

Fatty Alcohol(s)

The hair treatment compositions include an amount of fatty alcohol(s) typically in the range of about 0.1 to about 15 wt. %, based on the total weight of the hair treatment composition. For example, the amount of fatty alcohol(s) present in the hair treatment composition may range from about 0.1 to about 15 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %; about 1 to about 15 wt. %, about 1 to about 10 wt. %, about 1 to about 8 wt. %, about 1 to about 6 wt. %, about 1 to about 5 wt. %, about 1 to about 4 wt. %, about 1 to about 3 wt. %; about 1.5 to about 15 wt. %, about 1.5 to about 10 wt. %, about 1.5 to about 8 wt. %, about 1.5 to about 6 wt. %, about 1.5 to about 5 wt. %, about 1.5 to about 4 wt. %; about 2 to about 15 wt. %, about 2 to about 10 wt. %, about 2 to about 8 wt. %, about 2 to about 6 wt. %, about 2 to about 5 wt. %, about 2 to about 4 wt. %; about 2.5 to about 15 wt. %, about 2.5 to about 10 wt. %, about 2.5 to about 8 wt. %, about 2.5 to about 6 wt. %, about 2.5 to about 5 wt. %, or about 2.5 to about 4 wt. %, including all ranges and sub-ranges therebetween, based on the total weight of the hair treatment composition.

The fatty alcohols may be chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof.

More generally, the fatty alcohols may be liquid at 25° C., 1 atm, or may even be solid. They may even be glycerolated and/or oxyalkylenated, and may include from 8 to 30 carbon atoms. They may be saturated or unsaturated. For example, the fatty alcohols may be chosen from those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, cetyl alcohol, stearyl alcohol, cetearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of myristyl alcohol, cetyl alcohol, stearyl alcohol, isostearyl alcohol, oleyl alcohol, isotridecyl alcohol, and a mixture thereof.

The saturated liquid fatty alcohols may be branched. They can optionally comprise, in their structure, at least one aromatic or non-aromatic ring, but are preferably acyclic. Non-limiting examples of liquid saturated fatty alcohols include octyldodecanol, isostearyl alcohol, and 2-hexyldecanol.

The unsaturated liquid fatty alcohols may include in their structure at least one double or triple bond and, in some instances, one or more double bonds. When several double bonds are present, there are preferably 2 or 3 of them and they can be conjugated or non-conjugated. These unsaturated fatty alcohols can be linear or branched. They can optionally include in their structure at least one aromatic or non-aromatic ring but they are preferably acyclic. Among liquid unsaturated fatty alcohols, oleyl alcohol, linoleyl alcohol, linolenyl alcohol and undecylenyl alcohol can be cited.

Non-limiting examples of solid fatty alcohols include linear or branched, saturated or unsaturated alcohols containing from 8 to 30 carbon atoms, for example, myristyl alcohol, cetyl alcohol, stearyl alcohol, and cetearyl alcohol.

Non-limiting examples of high melting point fatty compounds include fatty alcohols such as, for example, myristyl alcohol (having a melting point of about 38° C.), cetyl alcohol (having a melting point of about 56° C.), stearyl alcohol (having a melting point of about 58-59° C.), behenyl alcohol (having a melting point of about 71° C.), and mixtures thereof. These compounds are known to have the above melting points. However, they often have lower melting points when supplied, since such supplied products are often mixtures of fatty alcohols having alkyl chain length distribution in which the main alkyl chain is cetyl, stearyl or behenyl group. In the present disclosure, more preferred fatty alcohols are myristyl alcohol, cetyl alcohol, stearyl alcohol and mixtures thereof.

Water

The hair treatment composition typically includes 10 wt. % or less of water. For example, the amount of water present in the cosmetic composition prior to combination with extraneous water may be 10 wt. % or less, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, or 0.5 wt. % or less, based on the total weight of the hair treatment composition. In some instances, the water present in the cosmetic composition prior to combination with extraneous water is added to the composition ("added water"). In some instances, the water present in the cosmetic composition prior to combination with extraneous water is not "added water," i.e., it is present in the cosmetic composition as part of a raw material that is included in the cosmetic composition. Although the cosmetic composition may include water prior to the combination of extraneous water, in some embodiments the cosmetic composition is anhydrous or substantially anhydrous.

Film Formers

The hair treatment composition may, optionally, include film-former(s). The film former is typically a hydrophobic material that imparts film forming and/or waterproofing characteristics. One such agent is polyethylene, which is available from New Phase Technologies as Performalene® 400, a polyethylene having a molecular weight of 400. Another suitable film former is polyethylene 2000 (molecular weight of 2000), which is available from New Phase Technologies as Performalene®. Yet, another suitable film former is synthetic wax, also available from New Phase Technologies as Performa® V-825. Other typical film-formers include acrylates/acrylamide copolymer, acrylates copolymer, acrylates/$C_{12}$-$C_{22}$ alkylmethacrylate copolymer, polyethylene, waxes, VP/dimethiconylacrylate/polycarbamylpolyglycol ester, butylated PVP, PVP/hexadecene copolymer, octadecene/MA copolymer, PVP/eicosene copolymer, tricontanyl PVP, Brassica Campestris/Aleuritis Fordi Oil copolymer, decamethyl cyclopentasiloxane (and) trimethylsiloxysilicate, and mixtures thereof. In some cases, the film former is VP/VA copolymer and/or acrylates/$C_{12}$-$C_{22}$ alkylmethacrylate copolymer, which is commercially available sold under the tradename Allianz OPT® by ISP.

A common film-former that is soluble in ethanol is Dermacryl LT or Dermacryl 79 marketed by Akzo Nobel (INCI Name: acrylates/octylacrylamide copolymner). Dermacryl LT (CAS Number: 80570-62-3) is a hydrophobic, high molecular weight carboxylated acrylic copolymer. It functions as a film-former in a broad range of cosmetic formulations, imparting waterproofing, increased occlusivity and decreased rub-off of actives.

The total amount of film-formers present in the hair treatment compositions may vary from, e.g., about 0.1 to about 5 wt. %, based on the total weight of the hair treatment composition. For example, the total amount of film-formers may be from about 0.1 to about 5 wt. %, about 0.1 to about 4 wt. %, about 0.1 to about 3 wt. %, about 0.1 to about 2 wt. %, about 0.1 to about 1 wt. %; about 0.5 to about 5 wt. %, about 0.5 to about 4 wt. %, about 0.5 to about 3 wt. %, about 0.5 to about 2 wt. %; about 0.7 to about 5 wt. %, about 0.7 to about 4 wt. %, about 0.7 to about 3 wt. %, about 0.7 to about 2 wt. %, including ranges and sub-ranges therebetween, based on the total weight of the hair treatment composition.

pH Adjuster(s)

The hair treatment composition may include one or more pH adjusters to increase or decrease the overall pH of the cosmetic composition. For example, one or more acids may be included to decrease the pH of the hair treatment composition. Examples of suitable acids for decreasing the pH of the hair treatment composition include, but are not limited to, citric acid, acetic acid, and the like. The hair treatment composition may include one or more bases, such as sodium hydroxide, potassium hydroxide and the like, to increase the pH of the hair treatment composition. Additional or alternative acids and bases that are suitable for adjusting the pH of the hair treatment composition are readily known to one of ordinary skill in the art.

The hair treatment composition may, desirably, have a pH of less than 7. For example, the cosmetic composition may have a pH of about 2 to less than 7, preferably about 2.5 to about 6 or about 3 to about 5.

The amount of the pH adjuster in the hair treatment composition may be based on the desired pH of the final hair treatment composition and/or product. For example, the total amount of the pH adjuster may range from about 0.05 to about 20 wt. %, based on the total weight of the hair treatment composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair treatment composition.

Methods of Treating Hair

Methods of treating hair according to the disclosure may vary but typically include applying a hair treatment composition as disclosed herein, allowing the hair treatment composition to remain on the hair for a sufficient amount of time, and rinsing the hair treatment compositions from the hair. The hair treatment composition may be applied to the hair in a sequence with other compositions. For example, the hair treatment composition may be applied to the hair before shampooing the hair, after shampooing the hair, before conditioning the hair, and/or after conditioning the hair, etc. The hair treatment compositions, however, are not required to be used in a sequence.

The methods may include applying an amount of the hair treatment composition onto the body, for example, onto one or both hands, onto the hair, onto the face, etc. The body may already be wet or damp with extraneous water or extraneous water can be included after the hair treatment composition has already been applied to the body. The hair treatment composition and the extraneous water may optionally be mixed together on the body to facilitate formation of an opaque emulsion having an increased viscosity. Alternatively, the hair treatment composition and extraneous water may be combined, and optionally mixed, prior to application to the body. For example, the hair treatment composition may be combined in a container, bowl, packaging, bottle, etc., and subsequently applied to the body after formation of the opaque emulsion.

In some instances, the methods include forming the opaque emulsion on the hands and subsequently applying the opaque emulsion to the hair. In other instances, the methods include forming an opaque emulsion directly on the hair. In yet other instance, the methods include forming an opaque emulsion other the face, or other parts of the body.

The hair treatment compositions and the emulsions formed by combination with water are useful for conditioning and/or managing the hair. The hair treatment compositions and the emulsions formed by combination of water can be applied to the wet or damp hair and may be massaged into the hair, for example, with the hands, and/or spread throughout the hair with a comb or brush. This results in a smoothing and softening of the hair, which reduces frizz, dryness, and unwanted volume.

Another unique aspect of the hair treatment compositions is that they may be used as a leave-on product. The hair treatment compositions can be applied to wet or damp hair and allowed to remain on the hair indefinitely, i.e., the hair treatment composition is not removed or rinsed from the hair prior to styling the hair.

In some cases, the hair treatment compositions are used in conjunction with additional hair-treatment compositions in a routine, for example, during an individual's normal showering/bathing routine. The hair treatment composition may be applied to the hair individually or may be combined with one or more additional compositions. Combining the compositions with one or more additional compositions (e.g., a shampoo, a conditioner, a rinse, etc.) can be useful for eliminating multiple steps from a routine. For instance, the hair treatment composition may be mixed with a shampoo (or conditioner) prior to application to the hair. In this case, the mixture of the shampoo (or conditioner) and the hair treatment composition are simultaneously applied to the hair during the cleansing or conditioning process and simultaneously rinsed from the hair. Alternatively, the hair treatment composition may be layered on top of (or lathered into) hair to which a shampoo (or conditioner) has already been applied or vice versa. In this case, the hair treatment composition may be applied to the hair and without rinsing it from the hair, a shampoo (or conditioner) is then subsequently applied to the hair. Alternatively, the shampoo (or conditioner) may be first applied to the hair and without rinsing the shampoo (or conditioner) from the hair, the hair treatment composition is also applied to the hair.

When used in conjunction with a shampoo and/or a conditioner, the hair treatment composition may be mixed or used with the shampoo and/or conditioner in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure:shampoo/conditioner, etc.).

The hair treatment compositions of the instant disclosure may be allowed to remain on the hair for a minimum amount of time before being rinsed from the hair, but it is not necessary to allow the hair treatment composition to remain on the hair for an extended period of time. Conveniently, the hair treatment compositions can be applied and allowed to remain on the hair for a period of time that is typical for regular shampooing and/or conditioning. For example, the hair treatment composition (whether combined with another hair-treatment composition such as a shampoo or conditioner) may be applied to the hair and allowed to remain on the hair for a few seconds (1, 2, 3, or 5 seconds) up to about 1 minute, about 2 minutes, about 5 minutes, about 10 minutes, about 15 minutes, about 20 minutes, about 25 minutes, or about 30 minutes.

When the hair treatment composition is not being mixed with another composition prior to application to the hair, the hair treatment composition may be applied to the hair immediately after or before the hair is treated with another composition (e.g., a shampoo and/or a conditioner). For example, the hair treatment compositions may be applied to the hair within about a few seconds or 1 minute, 2 minutes, 5 minutes, 10 minutes, or 20 minutes before or after a shampoo and/or a conditioner is applied to the hair.

The hair treatment compositions of the instant disclosure are unique in their ability to provide hair with improved manageability, shape/style, long-lasting style and frizz control, curl definition, curl retention, and smoothness. Accordingly, the instant disclosure relates to methods for treating hair, for example, for improving the manageability of hair, for imparting lasting style and frizz control, and for imparting smoothness and discipline. More specifically, the hair treatment compositions may be used in methods for conditioning the hair, providing curl definition to the hair, providing, manageability, providing frizz control to the hair, improving ease of combability and detangling, and providing smoothness and discipline.

Embodiments of the Disclosure

In certain embodiments, the hair treatment compositions of the instant disclosure include:
about 20 wt. % or more, preferably about 20 to about 85 wt. %, more preferably about 70 to about 85 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;
about 5 wt. % to about 50 wt. %, preferably about 5 to about 40 wt. %, more preferably about 10 to about 30 wt. %, of a monoalcohol having 1 to 10 carbons including, e.g., ethanol, propanol, butanol, pentanol, hexanol, isopropyl alcohol, cycohexanol, isobutyl alcohol, 2-methyl-2-butanol (2-methylbutan-2-ol), and a mixture thereof;

about 0.1 to about 5 wt. %, preferably about 0.1 to about 4 wt. %, more preferably about 0.1 to about 3 wt. %, of silicone, such as those chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, and mixtures thereof;

about 0.1 to about 10 wt. %, preferably about 0.1 to about 5 wt. %, more preferably about 0.1 to about 3 wt. %, of a cationic polymer, such as polyquaternium-67; and about 0.1 to about 10 wt. %, preferably about 0.1 to about 5 wt. %, more preferably about 0.5 to about 3 wt. %, of a cationic surfactant, e.g., selected from behentrimonium chloride, cetrimonium chloride, and a mixture thereof;

about 0.1 to about 15 wt. %, preferably about 1 to about 10 wt. %, more preferably about 1.5 to about 8 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof;

about 10 wt. % or less, preferably 8 wt. % or less, more preferably 6 wt. % or less, of water, wherein all percentages by weight are based on the total weight of the hair treatment composition.

In further embodiments, the hair treatment compositions of the instant disclosure include:

about 20 wt. % or more, preferably about 20 to about 85 wt. %, more preferably about 75 to about 85 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;

about 5 wt. % to about 40 wt. %, preferably about 5 to about 35 wt. %, more preferably about 10 to about 30 wt. %, of a monoalcohol having 1 to 10 carbons including, e.g., ethanol, propanol, butanol, pentanol, hexanol, isopropyl alcohol, cycohexanol, isobutyl alcohol, 2-methyl-2-butanol (2-methylbutan-2-ol), and a mixture thereof;

about 0.1 to about 5 wt. %, preferably about 0.1 to about 4 wt. %, more preferably about 0.1 to about 3 wt. %, of silicone, such as those chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, and mixtures thereof;

about 0.1 to about 5 wt. %, preferably about 0.1 to about 4 wt. %, more preferably about 0.1 to about 3 wt. %, of a polyquaternium-67; and about 0.1 to about 5 wt. %, preferably about 0.5 to about 5 wt. %, more preferably about 0.5 to about 3 wt. %, of a cationic surfactant, e.g., selected from behentrimonium chloride, cetrimonium chloride, and a mixture thereof;

about 0.1 to about 15 wt. %, preferably about 1 to about 10 wt. %, more preferably about 1.5 to about 8 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof;

about 5 wt. % or less, preferably 4 wt. % or less, more preferably 3 wt. % or less, of water, wherein the hair treatment composition is a translucent or clear composition until combined with extraneous water, whereupon the hair treatment composition forms an opaque emulsion in situ, wherein all percentages by weight are based on the total weight of the hair treatment composition before being combined with extraneous water.

In additional embodiments, a method is provided for treating hair including:

(i) optionally, applying a shampoo to the hair;

(ii) applying a hair treatment composition to hair, the hair treatment composition comprising:

about 20 wt. % or more, preferably about 20 to about 85 wt. %, more preferably about 70 to about 85 wt. %, of a polyol, such as those chosen from ethylene glycol, propylene glycol, butylene glycol, hexylene glycol, pentylene glycol, diethylene glycol, dipropylene glycol, 1,3 propanediol, glycerin, diglycerin, and a mixture thereof;

about 5 wt. % to about 50 wt. %, preferably about 5 to about 40 wt. %, more preferably about 10 to about 30 wt. %, of a monoalcohol having 1 to 10 carbons including, e.g., ethanol, propanol, butanol, pentanol, hexanol, isopropyl alcohol, cycohexanol, isobutyl alcohol, 2-methyl-2-butanol (2-methylbutan-2-ol), and a mixture thereof;

about 0.1 to about 5 wt. %, preferably about 0.1 to about 4 wt. %, more preferably about 0.1 to about 3 wt. %, of silicone, such as those chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, and mixtures thereof;

about 0.1 to about 10 wt. %, preferably about 0.1 to about 5 wt. %, more preferably about 0.1 to about 3 wt. %, of a cationic polymer, such as polyquaternium-67; and about 0.1 to about 10 wt. %, preferably about 0.1 to about 5 wt. %, more preferably about 0.5 to about 3 wt. %, of a cationic surfactant, e.g., selected from behentrimonium chloride, cetrimonium chloride, and a mixture thereof;

about 0.1 to about 15 wt. %, preferably about 1 to about 10 wt. %, more preferably about 1.5 to about 8 wt. %, of a fatty alcohol, such as those chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, myricyl alcohol and a mixture thereof;

about 10 wt. % or less, preferably 8 wt. % or less, more preferably 6 wt. % or less, of water,
wherein all percentages by weight are based on the total weight of the hair treatment composition;
(iii) optionally, applying a conditioner to the hair; and
(iv) optionally, rinsing the hair treatment composition from the hair.

EXAMPLES

Implementation of the present disclosure is provided by way of the following examples. The following examples serve to elucidate aspects of the technology without being limiting in nature.

Example 1

| | | INCI | Ex. A | Ex. B | Ex. C | Ex. D |
|---|---|---|---|---|---|---|
| (a) | Polyol | PROPYLENE GLYCOL, DIPROPYLENE GLYCOL, and GLYCERIN | 79.94 | 84.07 | 71.69 | 71.49 |
| (b) | Monoalcohol | ETHANOL, ISOPROPYL ALCOHOL, and/or BENZYL ALCOHOL | 10.22 | 10.14 | 20.14 | 20.14 |
| (c) | Silicone* | AMODIMETHICONE and/or SILICONE QUATERNIUM-18* | 0.34 | 0.25 | 0.34 | 0.34 |
| (d) | Cationic Polymer | POLYQUATERNIUM-67 | 0.3 | 0.2 | 0.3 | 0.3 |
| (e) | Cationic surfactant | BEHENTRIMONIUM CHLORIDE and CETRIMONIUM CHLORIDE | 1.35 | 0.74 | 1.19 | 1.19 |
| (f) | Fatty Alcohol | MYRISTYL ALCOHOL CETYL ALCOHOL | 3 | 2.7 | 2 | 1 1.13 |
| | Surfactants | ONE OR MORE OF C11-15 PARETH-7, LAURETH-9, TRIDECETH-3, TRIDECETH-10 TRIDECETH-6, TRIDECETH-12, STEARETH-6, and/or DECETH-7 | <0.5 | <0.5 | <0.5 | <0.5 |
| | Emollient | DICAPRYLYL CARBONATE | 0.90 | | | |
| (h) | Film former | VP/VA COPOLYMER | | | 0.45 | 0.45 |
| | Fragrance | FRAGRANCE | 1 | 1 | 1 | 1 |
| | Miscellaneous (Preservative, pH adjusters, etc.) | POTASSIUM SORBATE, TOCOPHEROL, PHENOXYETHANOL, SORBIC ACID, ACETIC ACID, and/or SALICYLIC ACID | <0.1 | <0.1 | <0.1 | <0.1 |
| (g) | Water | WATER | 2.72 | 0.78 | 0.88 | 0.97 |

*Silicone is included in the formula examples in the form of an emulsion that further comprises up to 5 wt. % of a surfactant, for example, nonionic surfactants, cationic surfactants, amphoteric surfactants, anionic surfactants such as C11-15 Pareth-7, laureth-9, trideceth-6, deceth-7, cocamidopropyl betaine, and/or trideceth-12.

Example 2

| | | INCI | Comp. A | Comp. B |
|---|---|---|---|---|
| (a) | Polyol | PROPYLENE GLYCOL | 82.65 | 72.95 |
| (b) | Monoalcohol | ETHANOL and ISOPROPYL ALCOHOL | 10.14 | 20.14 |
| (c) | Silicone | AMODIMETHICONE DIMETHICONE | — | — |
| (d) | Cationic Polymer | POLYQUATERNIUM-67 | 0.3 | |
| (e) | Cationic Surfactant | CETRIMONIUM CHLORIDE and BEHENTRIMONIUM CHLORIDE | 1.2 | 1.2 |
| (f) | Fatty Alcohol | MYRISTYL ALCOHOL | 2 | 2 |
| | Emollient | DICAPRYLYL CARBONATE | 0.9 | 0.9 |
| | Fragrance | FRAGRANCE | 1 | 1 |
| | Preservative | TOCOPHEROL | <0.01 | <0.01 |
| | Water | WATER | 1.82 | 1.8 |

Example 3

In this prophetic Example, the contact angle on hair fibers can be evaluated in order to evaluate or measure the hydrophobic nature of hair after being treated with the compositions of the invention. It is expected that the results can be correlated or linked to the degree of silicone deposition on hair. Without being limited to any specific theory, it is believed that the higher the contact angle, the higher the amount of silicone deposited on the hair, which is indicative of the efficacy of the hair treatment composition in delivering the conditioning benefits of silicones to the hair. For example, a 1 gram sample of the hair treatment composition can be applied onto a 2.7 g of wet, medium bleached hair swatch, which is then subsequently rinsed and dried, and then assessed using an Attension optical tensiometer in sessile drop mode. The swatch can then be tested with 3 droplets of the sample deposited in the midsection of the hair swatches. The average contact angle can then be obtained.

Example 4

Exemplary Composition A was evaluated in comparison to Comparative Composition B. Expert evaluators applied Exemplary Composition A and Comparative Composition B to 4 individuals for this evaluation. Specifically, the expert evaluators applied Exemplary Composition A to a first half of an individual's head of hair and applied Comparative Composition B to the second half of the individual's head of hair.

Exemplary Composition A provided faster transformation to hair fiber, better distribution, detangling, smoothness and more on-surface effect during product application than Comparative Composition B. In wet stage, Exemplary Composition A was better in detangling, and mass and slightly less supple compared to Comparative Composition B. In dry stage, Exemplary Composition A was better in shape, discipline, mass, lightweight, supple, and smoothness than Comparative Composition B.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair cleansing compositions of the instant disclosure can be free or essentially free of all components and elements positively recited throughout the instant disclosure.

In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the hair cleansing composition by itself. For example, a hair cleansing composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

What is claimed is:

1. A hair treatment composition comprising:
    (a) about 20 wt. % or more of a polyol;
    (b) about 5 wt. % to about 50 wt. % of a monoalcohol having 1 to 10 carbons;
    (c) about 0.1 to about 5 wt. % of silicone;
    (d) about 0.1 to about 10 wt. % of a cationic polymer;
    (e) about 0.1 to about 10 wt. % of a cationic surfactant;
    (f) about 0.1 to about 15 wt. % of a fatty alcohol; and
    (g) about 10 wt. % or less of water,
        wherein all percentages by weight are based on the total weight of the hair treatment composition.

2. The hair treatment composition of claim 1, wherein the hair treatment composition is a translucent or clear composition until combined with extraneous water, whereupon the hair treatment composition forms an opaque emulsion in situ.

3. The hair treatment composition of claim 2, wherein hair treatment composition has a viscosity of about 1 mPa.S to about 10,000 mPa.S at 25° C. at a shear rate of $1s^{-1}$ before combination with extraneous water.

4. The hair treatment composition of claim 1, wherein a weight ratio of the polyol to the monoalcohol is from 20:1 to 1:1.

5. The hair treatment composition of claim 1, wherein the polyol is chosen from ethylene glycol, propylene glycol, butylene glycol, hexylene glycol, pentylene glycol, diethylene glycol, dipropylene glycol, 1,3 propanediol, glycerin, diglycerin, polyethylene glycols, and a mixture thereof.

6. The hair treatment composition of claim 1, wherein the monoalcohol having 1 to 10 carbons is chosen from ethanol, propanol, butanol, pentanol, hexanol, isopropyl alcohol, cyclohexanol, isobutyl alcohol, 2-methyl-2-butanol (2-methylbutan-2-ol), and a mixture thereof.

7. The hair treatment composition of claim 1, wherein the silicone is chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), dimethicone copolyols, dimethicone copolyol esters, dimethicone copolyol quaternium nitrogen containing compounds, dimethicone copolyol phosphate esters, silicone quaternium-18, and mixtures thereof.

8. The hair treatment composition of claim 1, wherein the cationic polymer is a polyquaternium chosen from polyquaternium-1; polyquaternium-2; polyquaternium-4; polyquaternium-5; polyquaternium-6; polyquaternium-7; polyquaternium-8; polyquaternium-9; polyquaternium-10; polyquaternium-11; polyquaternium-12; polyquaternium-13; polyquaternium-14, polyquaternium-15; polyquaternium-16; polyquaternium-17; polyquaternium-18; polyquaternium-19; polyquaternium-20; polyquaternium-22; polyquaternium-24; polyquaternium-27; polyquaternium-28; polyquaternium-29; polyquaternium-30; polyquaternium-31 polyquaternium-32; polyquaternium-33; polyquaternium-34; polyquaternium-35; polyquaternium-36; polyquaternium-37; polyquaternium-39; polyquaternium-42; polyquaternium-43; polyquaternium-44; polyquaternium-45; polyquaternium-46; polyquaternium-47; polyquaternium-67; and mixtures thereof.

9. The hair treatment composition of claim 8, wherein the cationic polymer is polyquaternium-67.

10. The hair treatment composition of claim 1, wherein the cationic surfactant is chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

11. The hair treatment composition of claim 1, wherein the fatty alcohol is chosen from decyl alcohol, undecyl alcohol, dodecyl alcohol, myristyl alcohol, cetearyl alcohol, cetyl alcohol, stearyl alcohol, isostearyl alcohol, isocetyl alcohol, behenyl alcohol, linalool, oleyl alcohol, cis4-t-butylcyclohexanol, isotridecyl alcohol, or myricyl alcohol, and a mixture thereof.

12. The hair treatment composition of claim 1 further comprising:
(h) about 0.1 to about 5 wt. % of a film former.

13. The hair treatment composition of claim 2, wherein the silicone is suspended within the translucent or clear composition before being combined with extraneous water.

14. A hair treatment composition comprising:
(a) about 20 wt. % or more of a polyol;
(b) about 10 wt. % to about 40 wt. % of a monoalcohol having 1 to 10 carbons;
(c) about 0.1 to about 5 wt. % of silicone;
(d) about 0.1 to about 5 wt. % of a polyquaternium;
(e) about 0.5 to about 5 wt. % of a cationic surfactant;
(f) about 0.1 to about 15 wt. % of a fatty alcohol; and
(g) about 5 wt. % or less of water,
wherein the hair treatment composition is a translucent or clear composition until combined with extraneous water, whereupon the hair treatment composition forms an opaque emulsion in situ
wherein all percentages by weight are based on the total weight of the hair treatment composition before being combined with extraneous water.

15. The hair treatment composition of claim 14, wherein a weight ratio of the polyol to the monoalcohol is from 20:1 to 1:1.

16. The hair treatment composition of claim 14, wherein the polyol is chosen from propylene glycol, dipropylene glycol, butylene glycol, glycerin, or a mixture thereof.

17. A method for treating hair comprising:
(i) optionally, applying a shampoo to the hair;
(ii) applying a hair treatment composition to hair, the hair treatment composition comprising:
(a) about 20 wt. % or more of a polyol;
(b) about 5 wt. % to about 40 wt. % of a monoalcohol having 1 to 10 carbons;
(c) about 0.1 to about 5 wt. % of silicone;
(d) about 0.1 to about 5 wt. % of a cationic polymer; and
(e) about 0.1 to about 5 wt. % of a cationic surfactant;
(f) about 0.1 to about 15 wt. % of a fatty alcohol;
(g) about 10 wt. % or less of water,
wherein all percentages by weight are based on the total weight of the hair treatment composition;
(iii) optionally, applying a conditioner to the hair; and
(iv) optionally, rinsing the hair treatment composition from the hair.

18. The method of claim 17, wherein the hair treatment composition is a translucent or clear composition until combined with extraneous water, whereupon the hair treatment composition forms an opaque emulsion in situ.

19. The method of claim 17, wherein the hair treatment composition is:
mixing with a shampoo prior to application to hair;
layering onto hair with a shampoo;
applying to hair after a shampoo has been rinsed from the hair;
layering onto hair with a conditioner;
mixing with a conditioner prior to application to hair;
applying to hair after a conditioner has been rinsed from the hair;
mixing with a leave-in hair treatment prior to application to hair;
mixing with a mask composition prior to application to hair; or
applying to hair after a mask composition has been applied to and optionally, rinsed from the hair.

20. A method of claim 17, wherein the method:
conditions the hair; and/or
provides curl definition to the hair; and/or
provides frizz control to the hair; and/or
improves ease of combability and detangling; and/or
protects the hair from damage; and/or
increases the appearance of hair volume.

* * * * *